United States Patent [19]

Swanson et al.

[11] Patent Number: 4,556,146

[45] Date of Patent: Dec. 3, 1985

[54] INDIVIDUALLY PACKAGED DISPOSABLE ABSORBENT ARTICLE

[75] Inventors: James L. Swanson, West Chester, Ohio; Raymond L. Bendure, Kobe, Japan

[73] Assignee: The Procter & Gamble Company, Cincinnati, Ohio

[21] Appl. No.: 578,247

[22] Filed: Feb. 8, 1984

[51] Int. Cl.⁴ .............................................. A61F 13/16
[52] U.S. Cl. .................................... 206/440; 206/438; 604/385
[58] Field of Search ....................... 206/438, 440, 492; 229/87 A; 604/385

[56] References Cited

U.S. PATENT DOCUMENTS

| | | | |
|---|---|---|---|
| 1,352,962 | 9/1920 | Hitzigrath | 206/492 |
| 1,630,343 | 5/1927 | Hurlbut | 206/492 |
| 2,449,334 | 9/1948 | Smith | 229/87 R |
| 2,750,033 | 6/1956 | Pickens | 206/63.2 |
| 3,035,578 | 5/1962 | Elmore | 206/440 |
| 3,062,371 | 11/1962 | Patience | 206/440 |
| 3,193,181 | 7/1965 | Konjevich et al. | 229/87 |
| 3,561,593 | 2/1971 | Ruda | 229/87 R |
| 3,698,549 | 10/1972 | Glassman | 206/440 |
| 3,877,432 | 4/1975 | Gellert | 604/385 R |
| 3,963,029 | 6/1976 | Brooks | 604/385 R |
| 3,973,567 | 8/1976 | Srinivasan et al. | 128/290 |
| 4,286,639 | 9/1981 | Murphy | 206/440 |
| 4,402,689 | 9/1983 | Baum | 604/387 |

Primary Examiner—William T. Dixson, Jr.
Assistant Examiner—Brenda J. Ehrhardt
Attorney, Agent, or Firm—John M. Pollaro; Fredrick H. Braun; Richard C. Witte

[57] ABSTRACT

An article of manufacture is disclosed for absorbing liquids, particularly body fluids such as menses. The disclosed article is disposable and has a wrapper associated therewith. The wrapper overlays one major surface of the article and by folding the article and sealing the wrapper, an individually packaged disposable absorbent article is provided.

6 Claims, 4 Drawing Figures

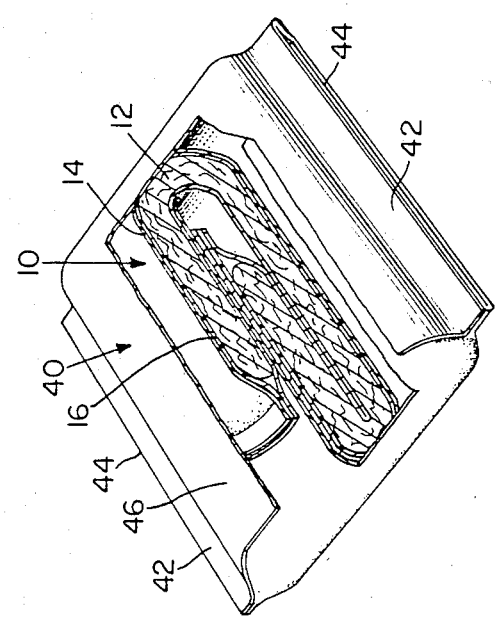
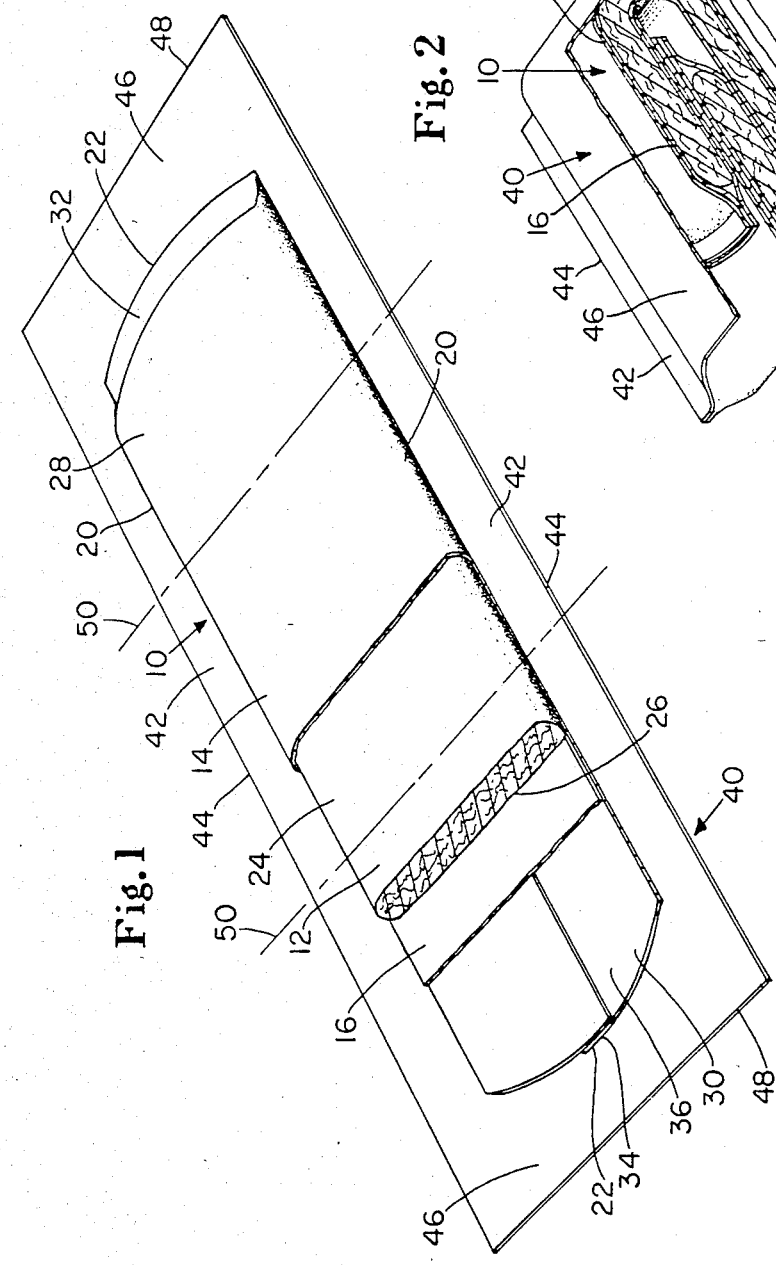

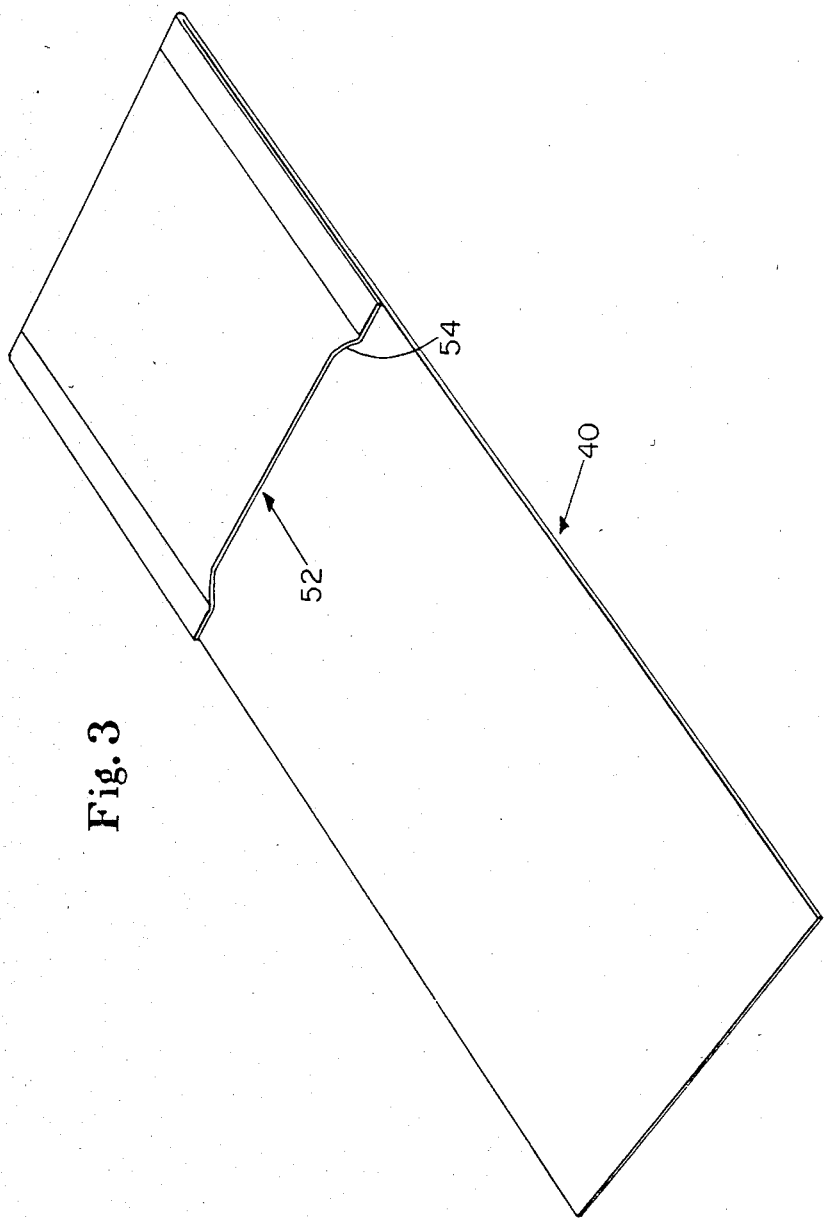

INDIVIDUALLY PACKAGED DISPOSABLE ABSORBENT ARTICLE

BACKGROUND OF THE INVENTION

This invention relates to disposable absorbent articles generally and more particularly relates to catamenial pads and the like. Still more particularly, this invention relates to catamenial pads which are individually packaged prior to use.

Disposable absorbent articles are well known in the prior art and have many uses. For example, disposable diapers are intended to absorb and retain urine; bandages are intended to absorb and retain blood and other body exudates; while catamenial pads are intended to absorb and retain menstrual fluids. In each instance, the disposable absorbent article absorbs and retains a liquid, thereby preventing the liquid from soiling, wetting, or otherwise contaminating the vicinity surrounding the point of liquid discharge.

In general, disposable absorbent articles all have the same basic structure which comprises an absorbent core encased within an envelope sheet. The envelope sheet has a liquid permeable, user-contacting topsheet portion with permits liquid to penetrate its thickness and contact the absorbent core where the liquid is retained. The prior art teaches numerous variations of and elements in addition to the basic absorbent core and envelope sheet arrangement, with each variation or additional element being directed to improving a specific characteristic of the disposable absorbent article.

While there are a great many variations in the specific structural features of disposable absorbent articles, they are frequently presented to the consumer in the U.S. in the same manner. Essentially, the disposable absorbent article, irrespective of what specific structural features are used, is packaged in a box or bag from which the consumer withdraws the ready-to-use article as needed. If the consumer needs only one article for later use, the consumer must take precautions to protect the article from soiling or contamination from the time it is removed from the box or bag until the aritcle is used. This is a particular problem with respect to catamenial pads. For example, if a woman wanted to carry a catamenial pad with her for use away from home, she would have to take precautions to insure that the pad was not damaged or soiled when carried in her purse or pocket.

The problem of protecting the disposable absorbent article once it is removed from the package in which it is sold has been addressed in the prior art. Bandages, for example, are commonly packaged individually and sold to the consumer in some sort of container which holds a convenient number of the individually packaged articles. In some countries, notably Japan, catamenial pads are likewise individually packaged and sold to the consumer in a container holding a convenient number of the individually packaged articles. In addition, U.S. Pat. No. 2,750,033 entitled Napkin Packaging which issued to J. B. Pickens on June 12, 1956 and U.S. Pat. No. 3,973,567 entitled Wrapped Sanitary Napkins which issued to S. S. Srinivasan et al on Aug. 10, 1976 disclose examples of individually packaged catamenial pads.

The patent to Pickens describes a bag type arrangement which contains the catamenial pad and the Srinivasan patent describes a sheet of material which is wrapped about the catamenial pad. The individually packaged catamenial pads may then be sold to the consumer in a convenient box or bag. In both the Pickens and Srinivasan et al patents, the protective wrap may also be used to provide a means for disposing of the used catamenial pad in a sanitary manner.

The individually packaged disposable absorbent articles of the prior art lack the aspects of the present invention whereby a wrapper overlays only one major surface of the disposable absorbent article and by folding the article and the wrapper as a unit, the wrapper may be sealed thereby providing an individually packaged disposable absorbent article.

It is therefore an object of the present invention to provide an individually packaged disposable absorbent article in which the wrapper overlays only one major surface of the disposable absorbent article.

A further object of the present invention is to provide an individually packaged disposable absorbent article in which the wrapper has an article facing surface and in which the article facing surface is in face to face relation with only one major surface of the disposable absorbent article.

A still further object of the present invention is to provide an individually packaged disposable absorbent article in which the wrapper has a pouch for receiving the used article thereby providing a means for conveniently and sanitarily disposing of the used article.

A still further object of the present invention is to provide an individually packaged disposable absorbent article in which the wrapper overlays the adhesive element thereby eliminating the need to provide a release paper.

These and other objects of the invention will be more readily apparent when considered in reference to the following description and when taken in connection with the accompanying drawings.

SUMMARY OF THE INVENTION

According to the present invention, a disposable absorbant article, such as a catamenial pad, is manufactured according to the teachings of the prior art. The catamenial pad is associated with a wrapper which overlays one major surface of the catamenial pad.

The wrapper extends beyond the perimeter of the disposable absorbent article so that when the disposable absorbent article and the wrapper are folded as a unit, the longitudinal side flaps of the wrapper may be frangibly sealed thereby providing the disposable absorbent article with an individual package.

The wrapper may be provided with a pouch which is readily formed by overlaying at least a portion of the wrapper with a sheet of liquid impermeable material which is affixed to the wrapper on three sides. The pouch may be conveniently used to receive the used disposable absorbent article thereby providing a convenient and sanitary means for disposing of the article.

BRIEF DESCRIPTION OF THE DRAWINGS

FIG. 1 is a partially cut away perspective view of a catamenial pad and its associated wrapper prior to being folded and sealed.

FIG. 2 is a partially cut away perspective view of a catamenial pad and its associated wrapper after they have been folded and sealed.

FIG. 3 is a perspective view of a wrapper having a pouch.

DESCRIPTION OF A PREFERRED EMBODIMENT

Figure 4:
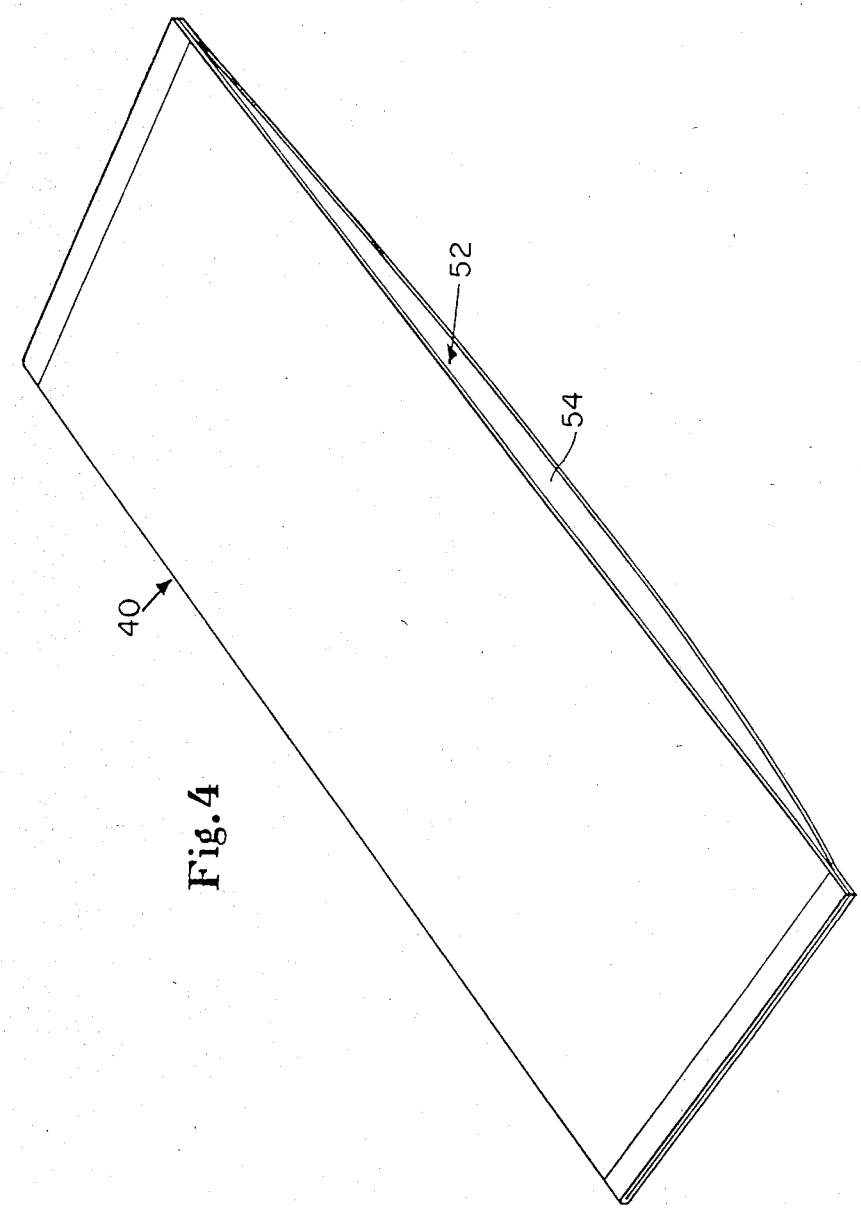
FIG. 4 is a perspective view of a wrapper having an alternative pouch configuration.

Referring now to the drawings there is shown an individually packaged disposable absorbent article embodying the teachings of the present invention. As used herein the term "absorbent article" refers to those articles intended to absorb and retain liquid and in particular to those articles which are placed against or in proximity to a wearer's body to absorb and contain the various liquids discharged from the body (e.g. blood, menses, urine). A "disposable absorbent article" is an absorbent article which is intended to be discarded after a single use (i.e., they are not intended to be laundered or otherwise restored and reused).

FIG. 1 is a partially cut away perspective view of a catamenial pad 10 and a wrapper 40 prior to being folded and sealed as set forth in greater detail herein below. A catamenial pad is a disposable absorbent article which is worn by females external to and in the proximity of the urogenital region and which is intended to absorb and contain menstrual fluids and other vaginal discharges. As used herein the term "catamenial pad" includes pantiliners which are worn by females external to the urogenital region between periods of heavy menstrual flow and which are intended to absorb light menstrual flow and nonmenstrual vaginal discharges. The primary difference between catamenial pads used during periods of heavy menstrual flow and catamenial pads used between periods of heavy menstrual flow (i.e., pantiliners) being the absorbent capacity of the pad.

While the present invention will be described with reference to a catamenial pad, it should be understood that the present invention has application in the context of other disposable absorbent articles such as diapers and bandages. Further, the teachings of this invention have application to catamenial pads manufactured according to the teachings of any of the multitudinous references in the catamenial pad art. A typical catamenial pad embodiment will now be described briefly.

As can be seen in FIG. 1, the catamenial pad 10 basically comprises an absorbent pad 12 an envelope sheet 14 and a barrier 16. The catamenial pad 10 has a perimeter generally comprising longitudinal perimeter segments 20 and transverse perimeter segments 22. The perimeter defines the outer boundary of the catamenial pad 10, while the longitudinal perimeter segments 20 and the transverse perimeter segments 22 define the outer boundary of the catamenial pad 10 along each longitudinal side and each transverse end respectively.

The absorbent pad 12 is compressible, conformable, and non-irritating to the user's skin and may be manufactured from a wide variety of absorbent materials which are capable of absorbing and retaining liquids. For example, a batt of absorbent fibers, a multiplicity of plies of creped cellulose wadding, or any equivalent material may be used. The absorbent capacity of the material used, however, must be sufficient to absorb and retain the expected liquid loading in the intended use of the absorbent article without undue bulk. In a preferred embodiment of the catamenial pad 10, intended to receive heavy menstrual discharges of approximately 40 millileters, about 8 grams of comminuted wood pulp, generally referred to as airfelt was used with good results.

The shape and dimensions of the absorbent pad 12 are selected to permit the disposable absorbent article to conform to and fit about the portion of the body against which it will be placed. Often, as in the preferred embodiment illustrated, the general shape and dimensions of the catamenial pad 10 will be determined by the shape and dimensions of the absorbent pad 12. In the preferred embodiment illustrated in the figures, the shape and dimensions of the absorbent pad 12 were selected to permit the catamenial pad 10 to conform to the urogenital region of the wearer's body. While the shape and dimensions of the absorbent pad 12 may be varied, it has been found that a generally planar configuration having a first major surface 24 and a second major surface 26 is preferable. The first major surface 24 is that surface of the absorbent pad 12 facing toward the source of liquid (i.e. toward the wearer's body) and the second major surface 26 is that surface of the absorbent pad 12 facing away from the source of liquid. In the preferred catamenial pad 10 illustrated, a generally rectangular, planar shaped absorbent pad 12 having a length of about 9.0 inches (22.9 centimeters) and a width of about 2.5 inches (6.4 centimeters) was used with good results. It should be understood, however, that other shapes (e.g. elongated ovals, triangles, squares, etc.) and other dimensions may be used, particularly in absorbent articles other than catamenial pads.

The envelope sheet 14 encases the absorbent pad 12 and is preferably compliant, soft feeling, and non-irritating to the wearer's body. The envelope sheet 14 helps maintain the structural integrity of the absorbent pad 12 and has a first and a second end flap 30 and 32 respectively. The envelope sheet 14 is wrapped about the absorbent pad 12 and is affixed to itself along a seam 34 which is adjacent the second major surface 26 and which traverses the catamenial pad 10 longitudinally. The first and second flaps 30 and 32 respectively extend beyond the transverse ends of the absorbent pad 12 and are preferably sealed so as to completely encase the absorbent pad 12 within the envelope sheet 14. The portion of the envelope sheet 14 overlaying the first major surface 24 is the topsheet portion 28 and the portion of the envelope sheet 14 overlaying the second major surface 26 is the backsheet portion 36 of the envelope sheet 14. The topsheet portion 28 is liquid permeable. In use the topsheet portion 28 contacts the skin of the catamenial pad wearer and permits the rapid transmission of liquid through its thickness to the absorbent pad 12 where the liquid is retained.

There are many suitable materials from which the envelope sheet 14 may be manufactured. The topsheet portion 28 may be manufactured from either hydrophobic or hydrophilic fibers and may, for example, be carded, spun bonded, melt blown, or air laid. Alternatively, the topsheet portion 28 may be a continuous film or sheet of, for example, thermoplastic material which is apetured. A suitable topsheet portion 28 is described in U.S. Pat. No. 4,324,246 which issued to Mullane et al on Apr. 13, 1982 which patent is incorporated herein by reference.

The topsheet portion 28 and the backsheet portion 36 may either be integral (i.e. the backsheet portion 36 and the topsheet portion 28 are separate elements affixed to each other) or unitary (i.e. the backsheet portion 36 and the topsheet portion 28 are formed from a continuous and undivided sheet of material) and may either have the same or different physical properties. The preferred embodiment of FIG. 1 shows the topsheet portion 28 and the backsheet portion 36 as being unitary and as having the same physical properties. Thus, the backsheet portion 36 is also liquid permeable.

To help prevent liquids absorbed by the absorbent pad 12 from penetrating through the backsheet portion 36, it is advantageous to interpose a barrier 16 at the interface between the second major surface 26 of the absorbent pad 12 and the backsheet portion 36. The barrier 16 may be manufactured from any flexible, liquid impermeable material which is non-irritating to the wearer. Preferably, the barrier 16 is a sheet of polyethylene which is coincident with the backsheet portion 36.

Alternatively, the envelope sheet 14 may comprise a liquid permeable topsheet portion and a liquid impermeable backsheet portion which are made integral with each other by affixing them together about their periphery.

It is common to provide the catamenial pad 10 with an adhesive element (not shown). The adhesive element is positioned on the backsheet portion 36 and, in use, serves to affix the catamenial pad 10 to the wearer's undergarments thereby maintaining the catamenial pad 10 in place against the wearer's body. The adhesive element may take the form of a coating of adhesive which is in strips or any other suitable pattern. Preferably the backsheet portion 36 is coated uniformly with a layer of a pressure sensitive hot melt adhesive such as NS34-2823 as manufactured by National Starch and Chemical of Bridgewater, N.J.

In accordance with the teachings of this invention, a wrapper 40 is associated with, and has dimensions generally larger than those of the catamenial pad 10. Thus, the wrapper 40 has longitudinal flap portions 42 comprising that portion of the wrapper 40 between the longitudinal edge 44 of the wrapper and the longitudinal perimeter segment 20 of the catamenial pad 10. In the preferred embodiment illustrated in FIG. 1, the wrapper 40 also has transverse flap portions 46 comprising that portion of the wrapper 40 between the transverse edges 48 of the wrapper 40 and the transverse perimeter segments 22 of the catamenial pad 10. The wrapper 40 is manufactured from a thin flexible material which is preferably liquid impermeable. For example, polyethylene films have been found suitable.

The wrapper 40 overlays the backsheet portion 36 with the longitudinal flap portions 42 extending beyond the longitudinal perimeter segments 20. It is important to note that the wrapper 40 is not folded onto or otherwise brought into contact with the topsheet portion 28. In other words, the surface of the wrapper 40 facing the backsheet portion 36 is in face to face relation with the backsheet portion 36 only. The wrapper 40 may be releasably affixed to the catamenial pad 10 by the aforementioned adhesive element. If an adhesive element is used in this manner, it is not necessary to provide the absorbent article with a separate release paper as is commonly done in prior art devices. As used herein, the term "release paper" refers to any sheet material used to protect the adhesive element from contamination prior to use.

To individually package the catamenial pad 10, the catamenial pad 10 and the affixed wrapper 40 are folded as a unit. That is, they are folded together with the wrapper 40 remaining in place with respect to the catamenial pad 10. Preferably, the catamenial pad 10 is folded lengthwise into thirds about two fold-axes 50, as shown in FIG. 2. The longitudinal flap portions 42 are frangibly sealed using any of the well-known sealing techniques. For example, the longitudinal flap portions 42 may be heat sealed, glued, or ultrasonically bonded.

In use, the individually packaged catamenial pad is provided to a user. The user may then break the seals unfolds the catamenial pad 10 and separates the wrapper 40 from the catamenial pad 10. The catamenial pad 10 may then be used as such devices normally are.

FIG. 3 shows an alternatively preferred embodiment of the wrapper 40 provided with a pouch 52 for receiving a used disposable absorbent article. The pouch 52 is formed simply by affixing a pouch element 54 to the wrapper 40. The pouch element 54 is preferrably liquid impermeable and may be manufactured from the same material as the wrapper 40. The pouch element 54 is affixed to the wrapper along three sides using any suitable bonding means and is preferably heat sealed to the wrapper 40. Alternatively, as shown in FIGS. 3 and 4, the pouch element 54 may be unitary with the wrapper 40 requiring only the longitudinal sides of the pouch element 54 to be affixed to the wrapper 40. The pouch 52 receives the used catamenial pad 10 and provides a means for disposing of the catamenial pad 10 in a sanitary manner.

What is claimed is:

1. An individually packaged disposable absorbent article comprising:

an absorbent pad having a first major surface and a second major surface;

an envelope sheet comprising a liquid permeable topsheet portion overlaying said first major surface and a backsheet portion overlaying said second major surface said envelope sheet encasing said absorbent pad, said backsheet portion being coated with a layer of adhesive;

a perimeter having longitudinal perimeter segments; and a wrapper, said wrapper being releasably affixed to said backsheet portion of said envelope sheet and having longitudinal flap portions extending outward from said longitudinal perimeter segments, said absorbent pad and said wrapper being folded as a unit about at least two fold-axes and said longitudinal flap portions being frangibly sealed.

2. The individually packaged disposable absorbent article of claim 1 wherein said wrapper has a pouch.

3. The individually packaged disposable absorbent article of claim 1 wherein said backsheet portion and said topsheet portion are unitary and a barrier is interposed between said backsheet portion and said second major surface.

4. The individually packaged disposable absorbent article of claim 1 wherein said backsheet portion and said topsheet portion are integral; said backsheet portion being liquid impermeable.

5. An individually packaged catamenial pad comprising:

an absorbent pad having a first major surface and a second major surface;

an envelope sheet comprising a liquid permeable topsheet portion overlaying said first major surface and a backsheet portion overlaying said second major surface said envelope sheet encasing said absorbent pad, said backsheet portion being coated with a layer of adhesive;

a perimeter having longitudinal perimeter segments; and a wrapper, said wrapper being releasably affixed to said backsheet portion of said envelope sheet and having longitudinal flap portions extending outward from said longitudinal perimeter segments, said absorbent pad and said wrapper being folded as a unit about at least two fold-axes and said longitudinal flap portions being frangibly sealed.

6. The individually packaged catamenial pad of claim 5 wherein said wrapper has a pouch.

* * * * *